(12) United States Patent
Matsumura (10) Patent No.: US 10,555,842 B2
(45) Date of Patent: Feb. 11, 2020

(54) UNDERPANTS-TYPE DISPOSABLE DIAPER (71) Applicant: DAIO PAPER CORPORATION, Ehime (JP)

(72) Inventor: Takashi Matsumura, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 395 days.

(21) Appl. No.: 15/514,731

(22) PCT Filed: Sep. 28, 2015

(86) PCT No.: PCT/JP2015/077341
§ 371 (c)(1),
(2) Date: Mar. 27, 2017

(87) PCT Pub. No.: WO2016/052416
PCT Pub. Date: Apr. 7, 2016

(65) Prior Publication Data
US 2017/0239105 A1 Aug. 24, 2017

(30) Foreign Application Priority Data

Sep. 30, 2014 (JP) ................................ 2014-201328

(51) Int. Cl.
*A61F 13/49* (2006.01)
*A61F 13/515* (2006.01)
(Continued)

(52) U.S. Cl.
CPC ...... *A61F 13/49011* (2013.01); *A61F 13/496* (2013.01); *A61F 13/515* (2013.01);
(Continued)

(58) Field of Classification Search
CPC ............. A61F 13/49011; A61F 13/496; A61F 13/515; A61F 13/53; B29C 66/21
See application file for complete search history.

(56) References Cited

U.S. PATENT DOCUMENTS

2004/0133180 A1* 7/2004 Mori ................. A61F 13/15593
604/385.25
2010/0051170 A1* 3/2010 Nakakado ......... A61F 13/15593
156/73.1

FOREIGN PATENT DOCUMENTS

EP 3251644 A1 12/2017
JP 03-080859 A 4/1991
(Continued)

*Primary Examiner* — Ariana Zimbouski
(74) *Attorney, Agent, or Firm* — Muncy, Geissler, Olds & Lowe, P.C.

(57) ABSTRACT

The present invention is intended to improve a fit to the lower part of a gluteal region. The foregoing issue is solved by an underpants-type disposable diaper in which an outer body is formed by stacking an elastic sheet layer between a first sheet layer and a second sheet layer, when the elastic sheet layer is extended in a width direction, the first sheet layer and the second sheet layer are joined together directly or indirectly at a large number of dot-like joint portions arranged at intervals left in the width-direction and front-back direction, cover parts of the outer body of a back body have peripheral edge regions and surrounded regions surrounded by the peripheral edge regions, and the arrangement density of the dot-like joint portions in the peripheral edge regions is higher than the arrangement density of the dot-like joint portions in the surrounded regions.

6 Claims, 10 Drawing Sheets

(51) Int. Cl.
*A61F 13/496* (2006.01)
*A61F 13/53* (2006.01)

(52) U.S. Cl.
CPC .... *A61F 13/53* (2013.01); *A61F 2013/49074* (2013.01); *A61F 2013/49088* (2013.01); *A61F 2013/530481* (2013.01)

(56) References Cited

FOREIGN PATENT DOCUMENTS

| | | |
|---|---|---|
| JP | 2004-532758 A | 10/2004 |
| JP | 2012-050714 A | 3/2012 |
| JP | 4987967 B | 8/2012 |
| JP | 5292586 B | 9/2013 |
| WO | WO 2008/126708 A1 | 10/2008 |

\* cited by examiner

UNDERPANTS-TYPE DISPOSABLE DIAPER

TECHNICAL FIELD

The present invention relates to an underpants-type disposable diaper excellent in its fit to the bulge of a gluteal region.

An underpants-type disposable diaper includes an outer body forming individually or integrally a front body and a back body, and an inner body that has an absorber and is attached to the inner surface of the outer body from the front body to the back body. In general, the outer body of the front body and the outer body of the back body are joined together at the both sides to form side seal portions, thereby forming a waist opening and a pair of right and left leg openings.

BACKGROUND ART

The outer body has a waist part defined as a front-back direction range with the side seal portions (front-back direction area ranging from the waist opening to the upper ends of the leg openings) and an intermediate portion defined as a front-back direction range forming the leg openings. In general, the intermediate portion has cover parts positioned on the lateral sides of the inner body, and elastic members such as rubber threads or sheets are provided in the waist part and the cover parts (for example, refer to Patent Documents 1 and 2).

However, the conventional underpants-type disposable diapers have a problem of an insufficient fit to the lower part of a gluteal region. Specifically, the waist part of the outer body is entirely cylindrical, and when elastic members are provided in a state extended in a width direction to the waist part, the elastic members exert a contraction force to tighten the entire waist part and fit to the wearer's body without looseness. Meanwhile, the cover parts have width-direction outer ends (edges of the leg openings) made free, and are likely to be insufficient in their fit even when elastic members are provided in the extended state to the cover parts. In particular, the cover parts of the outer body in the back body are portions to cover the lower bulging part of a gluteal region, and the width-direction outer ends of the cover parts, that is, the edges of the leg openings are likely to lift and flap under influence of the bulge of the gluteal region.

To deal with this problem, providing elastic members along the edges of the leg openings has been proposed as described in Patent Document 1. However, the addition of the members would unfavorably increase manufacture costs and bring about reduction in flexibility and air permeability.

CITATION LIST

Patent Documents

Patent Document 1: Japanese Patent No. 4987967
Patent Document 2: Japanese Patent No. 5292586
Patent Document 3: JP-T No. 2004-532758

SUMMARY OF INVENTION

Technical Problem

A major object of the present invention is to improve a fit to the lower part of a gluteal region.

Solution to Problem

The present invention having solved the foregoing problem is as follows:

<The Invention of Claim 1>

An underpants-type disposable diaper comprising an outer body constituting individually or integrally a front body and a back body, and an absorber provided on the inner side of the outer body ranging from the front body to the back body, the outer body of the front body and the outer body of the back body being joined together at both side edges to form side seal portions, thereby forming a waist opening and a pair of right and left leg openings, wherein the outer body of the back body has a waist part defined as a front-back direction range having the side seal portions and an intermediate portion defined as the front-back direction range forming the leg openings, the intermediate portion has cover parts positioned closer to lateral sides than the inner body, the cover parts are formed at least by stacking an elastic sheet layer between a first sheet layer and a second sheet layer, when the elastic sheet layer is extended in a width direction, the first sheet layer and the second sheet layer are joined together directly or indirectly at a large number of dot-like joint portions arranged at intervals left in the width-direction and front-back direction, and at least an intermediate portions of the cover parts in the front-back direction are configured such that the arrangement density of the dot-like joint portions becomes higher stepwise or continuously from width-direction outer edges to a width-direction central side.

(Operation and Effect)

In the stretchable structure as in the present invention in which the elastic sheet layer is sandwiched in the state extended in the width direction between the first sheet layer and the second sheet layer and these layers are joined together at the large number of dot-like joint portions, the contraction rate becomes lower in the width direction with increase in the arrangement density of the dot-like joint portions. Accordingly, configuring at least the front-back direction intermediate portions of the cover parts such that the arrangement density of the dot-like joint portions becomes higher stepwise or continuously from width-direction outer edges to a width-direction center, the cover parts curve outward in a natural-length state, and even when the diaper is worn in a state extended to some extent, the curve is maintained to provide a favorable fit to the lower surface of the gluteal region. This makes it possible to improve the fit to the lower part of the gluteal even without providing elastic members along the edges of the leg openings.

<The Invention of Claim 2>

The underpants-type disposable diaper according to claim 1, wherein the cover parts have peripheral edge regions and surrounded regions surrounded by the peripheral edge regions, and the arrangement density of the dot-like joint portions in the peripheral edge regions is higher than the arrangement density of the dot-like joint portions in the surrounded regions.

(Operation and Effect)

In this mode, the surrounded regions curve and swell to the peripheral edge regions, and fit to the lower surface of the gluteal region. Accordingly, it is possible to improve the fit sufficiently by the simple structure in which the arrangement density is merely changed in two stages.

<The Invention of Claim 3>

The underpants-type disposable diaper according to claim 2, wherein the width-direction outer edges of at least front-back direction central side of the cover parts are linear or curved so as to be positioned closer to the inner body with increasing proximity to the front-back direction central side.
(Operation and Effect)

Shaping the edges of the cover parts in such a manner as described above would make more preferable the fit to the lower part of the gluteal region.

<The Invention of Claim 4>

The underpants-type disposable diaper according to any one of claims 1 to 3, wherein the front-back direction length of parts of the back body positioned on the lateral sides of the inner body is larger than the front-back direction length of parts of the front body positioned on the lateral sides of the inner body, and the cover parts have portions of the same width as the waist part on the waist part side.
(Operation and Effect)

The cover parts as described above are suitable in particular to the present invention because the edges of the leg openings are likely to lift and flap.

<The Invention of Claim 5>

The underpants-type disposable diaper according to any one of claims 1 to 4, wherein at least a front-back direction intermediate portion of the waist part of the outer body of the back body is configured such that the arrangement density of the dot-like joint points becomes higher stepwise or continuously from the width-direction outer edge to the width-direction central side.
(Operation and Effect)

Making a change in the arrangement density of the dot-like joint portions in the waist part as well would make it possible to improve the fit to not only the lower part but also a wider zone of the gluteal region including the lateral sides of up-down intermediate portion of the gluteal region.

<The Invention of Claim 6>

The underpants-type disposable diaper according to any one of claims 1 to 5, wherein the difference in the arrangement density of the dot-like joint portions is made by at least one of the difference in the areas of the individual dot-like joint portions and the difference in the intervals between the dot-like joint portions.
(Operation and Effect)

As described above, the difference in the density of the dot-like joint portions can be formed by at least one of the difference in the areas of the individual dot-like joint portions and the difference in the intervals between the dot-like joint portions.

Advantageous Effects of Invention

As described above, according to the present invention, it is possible to provide the advantage of improving the fit to the lower part of the gluteal region and others.

DESCRIPTION OF EMBODIMENT

One embodiment of the present invention will be described in detail with reference to the accompanying drawings. The dot patterns in the drawings represent a joining means such as a hot-melt adhesive.

FIGS. 1 to 7 illustrate an example of underpants-type disposable diaper. The underpants-type disposable diaper (hereinafter, also simply called diaper) has an integral outer body 20 constituting a front body F and a back body B and an inner body 10 fixed and integrated to the inner surface of the outer body 20. The inner body 10 is formed by interposing an absorber 13 between a liquid pervious face sheet 11 and a liquid impervious back sheet 12. At the time of manufacture, the back surface of the inner body 10 is joined to the inner surface (upper surface) of the outer body 20 by a joining means such as a hot-melt adhesive (as illustrated in the patterned part 10B of FIG. 7), then the inner body 10 and the outer body 20 are folded in the vertical (front-back direction) center as a boundary between the front body F and the back body B, and then their both side parts are joined together by heat welding, a hot-melt adhesive, or the like to form side seal portions 21, thereby obtaining the underpants-type disposable diaper with a waist opening and a pair of right and left leg openings.

(Structure Example of the Inner Body)

Figure 4:
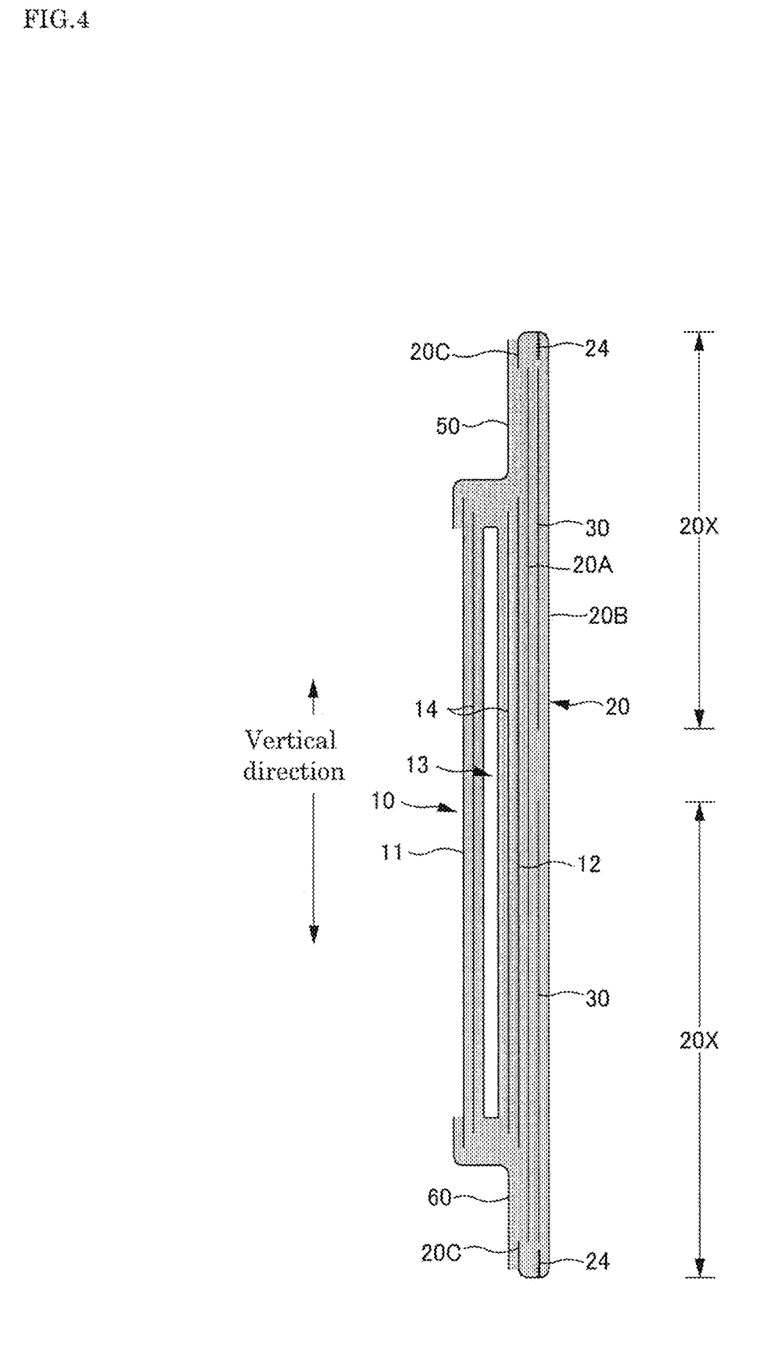
FIG. 4 is a cross-sectional view of FIG. 1 taken along line C-C.
Figure 5:
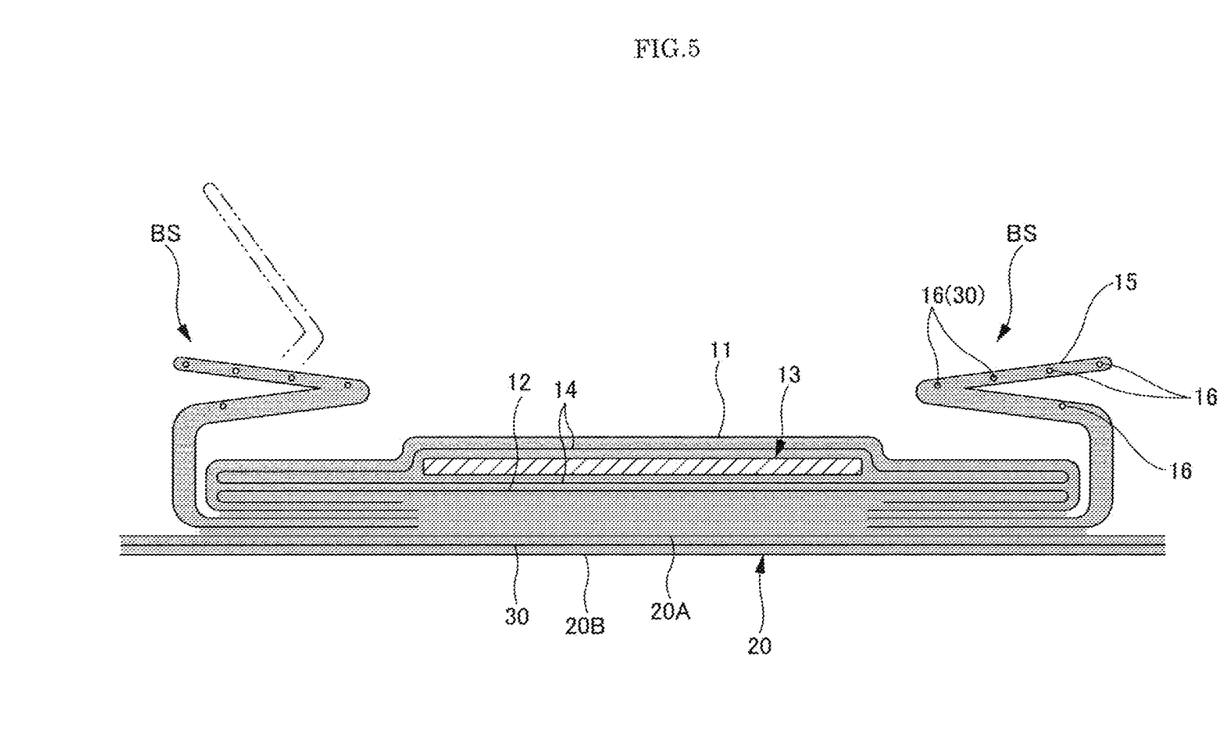
FIG. 5 is a cross-sectional view of FIG. 1 taken along line A-A.
Figure 6:
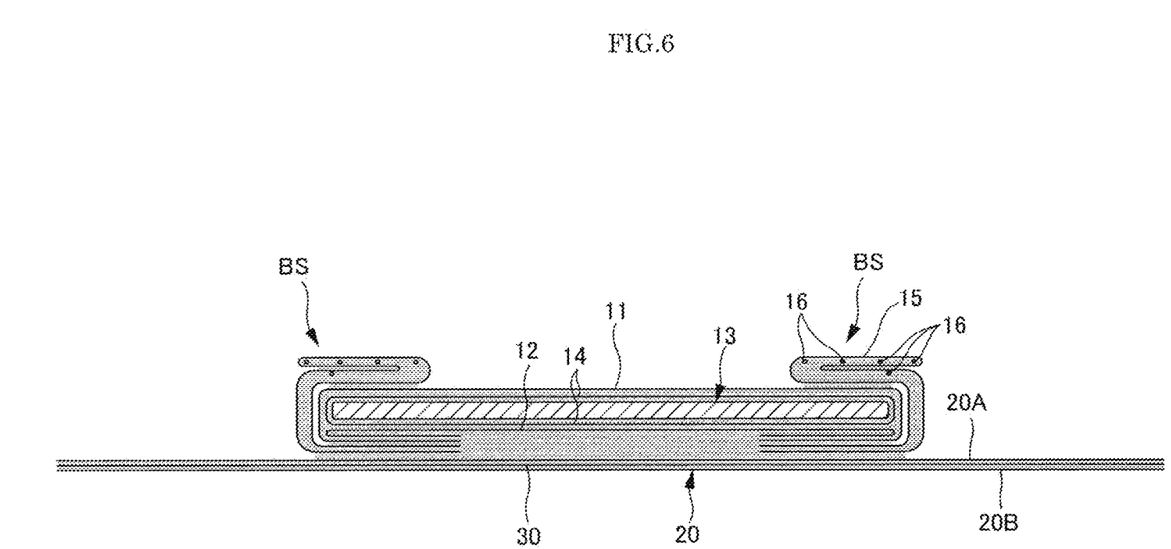
FIG. 6 is a cross-sectional view of FIG. 1 taken along line B-B.
Figure 7:
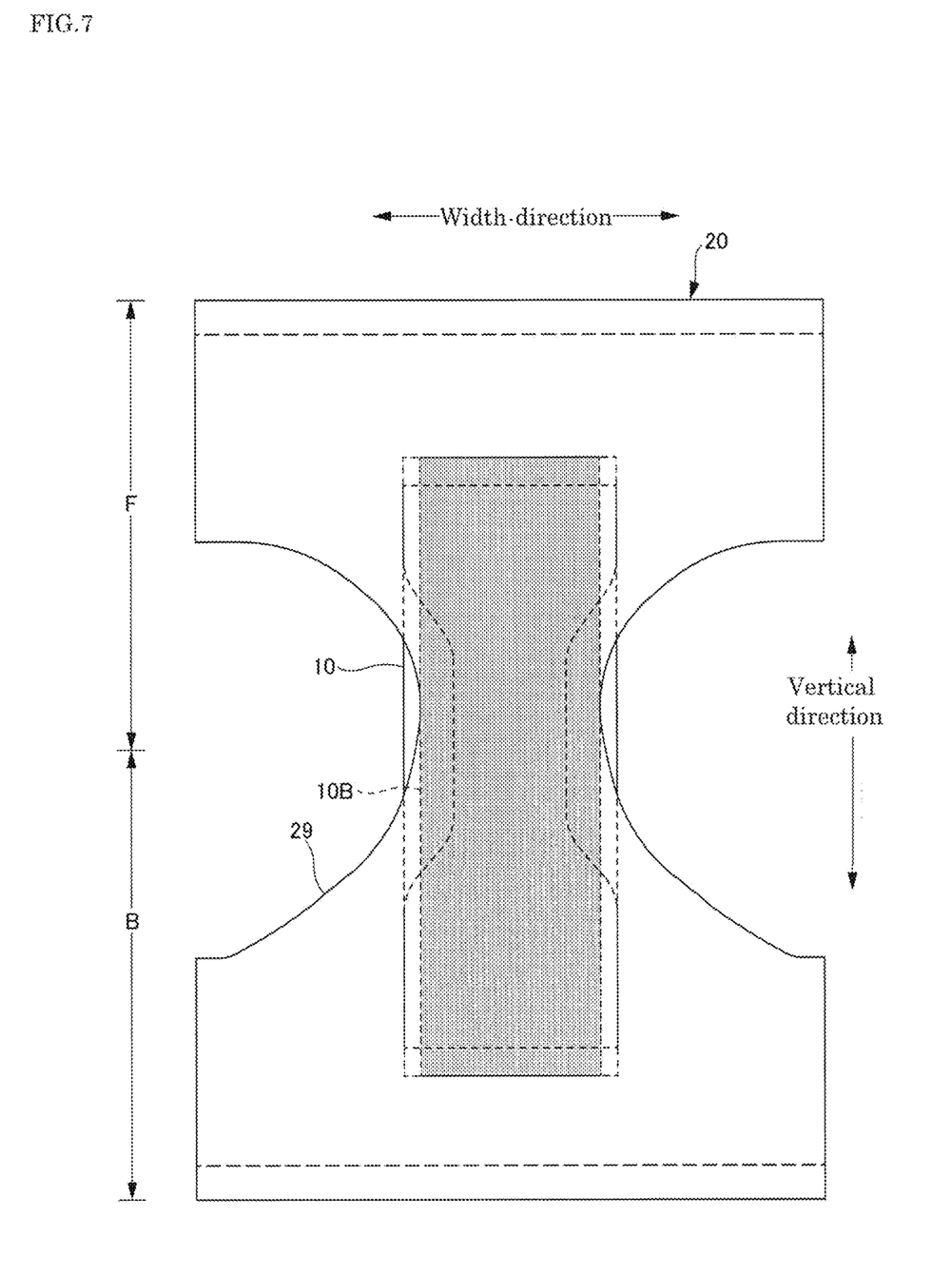
FIG. 7 is a plane view of the major components of the underpants-type disposable diaper in the opened state.

As illustrated in FIGS. 4 to 6, the inner body 10 is structured such that the absorber 13 is interposed between the liquid pervious face sheet 11 made of non-woven fabric or the like and the liquid impervious back sheet 12 made of polyethylene or the like. The inner body 10 is intended to absorb and hold excretion having passed through the face sheet 11. Although there is no particular limitation on the planar shape of the inner body 10, the inner body 10 is generally shaped in an approximate rectangle as in the illustrated drawing.

The liquid pervious face sheet 11 covering the external side (skin-contacting side) of the absorber 13 is preferably a porous or non-porous non-woven fabric sheet or a porous plastic sheet. The raw fibers for non-woven fabric may be synthetic fibers based on olefin such as polyethylene or polypropylene, or synthetic fibers based on polyester or polyamide, or reproduced fibers of rayon or cupra, natural fibers of cotton or the like. The non-woven fabric may be produced by any appropriate processing method such as spun-lacing, spun-bonding, thermal bonding, melt-blowing, or needle punching. Among these processing methods, the spun-lacing method is excellent for flexibility and drape properties, and the thermal bonding method is excellent for bulkiness and softness. Forming a large number of through holes in the liquid pervious face sheet 11 would allow quick absorption of urine and the like and produce an excellent feeling of dryness. The liquid pervious face sheet 11 wraps around the side edges of the absorber 13 and extends up to the back surface of the absorber 13.

The liquid impervious back sheet 12 covering the back side (non-skin-contacting side) of the absorber 13 is made of a liquid impervious plastic sheet of polyethylene, polypropylene, or the like. However, in recent years, the liquid impervious plastic sheets with moisture perviousness have been used preferably from the viewpoint of prevention of stuffiness. The liquid impervious and moisture pervious sheet is a microporous sheet that is obtained by melting and kneading an inorganic filling agent in an olefin resin such as polyethylene, polypropylene, or the like to form a sheet and then elongating the sheet in a uniaxial or biaxial direction, for example.

The absorber 13 is basically made from a publicly known material, for example, accumulated pulp fibers, a filament assembly of cellulose acetate or the like, or non-woven fabric. The absorber 13 may include as necessary high-absorbent polymer particles mixed and fixed thereto. The absorber 13 can be wrapped as necessary with a package sheet 14 with liquid perviousness and liquid retention such as crepe paper for retention of the shape and the polymer.

The absorber 13 is shaped like an approximately sand glass with a narrower part 13N smaller in width than the front and back sides of the crotch portion. However, the absorber 13 may have an arbitrary shape such as a rectangle. The dimensions of the narrower part 13N can be decided as appropriate. However, the front-back direction length of the narrower part 13N can be about 20 to 50% of the entire width of the diaper. The smallest width of the narrower part 13N can be about 40 to 60% of the entire width of the absorber 13. When the planar shape of the inner body 10 is an approximate rectangle with the narrower part 13N as described above, the inner body 10 has a remaining part formed without the absorber 13 corresponding to the narrower part 13N of the absorber 13.

The inner body 10 has three-dimensional gathers BS fitting to the legs on the both sides. As illustrated in FIGS. 5 and 6, each of the three-dimensional gathers BS is composed of a gather non-woven fabric 15 that is formed as a duplicate sheet by folding a fixation portion fixed to the side of the back surface of the inner body, a main unit portion extending from the fixation portion through the lateral side of the inner body to the side part of the front surface of the inner body, fallen portions formed by fixing the front-back ends of the main unit portion in a fallen state to the side parts of the front surface of the inner body, and a free portion formed by not fixing the portion between the fallen portions.

Elongated gather elastic members 16 are arranged at forward ends of the free portion in the duplicate sheet. The gather elastic members 16 are intended to raise the non-woven fabric portions protruding from the side edges of the absorber by their elastic stretching force as illustrated by the two-dot chain line in FIG. 5 to form the three-dimensional gathers BS in the product state.

The liquid impervious back sheet 12 is folded back together with the liquid pervious face sheet 11 on the width-direction both sides of the absorber 13. The liquid impervious back sheet 12 is desirably opaque so as not to allow the dark color of stool and urine to be seen through. To make the liquid impervious back sheet 12 opaque, plastic is preferably formed into a film with internal addition of a mixture of pigments and fillers such as calcium carbonate, titanium oxide, zinc oxide, white carbon, clay, talc, and barium sulfate.

The gather elastic members 16 can be made from a generally used material such as styrene-based rubber, olefin-based rubber, urethane-based rubber, ester-based rubber, polyurethane, polyethylene, polystyrene, styrene-butadiene, silicon, or polyester. To make the gather elastic members 16 hard to see from the outside, the gather elastic members 16 have a thickness of 925 dtex or less and are arranged under a tension of 150 to 350% at intervals of 7.0 mm or less. The gather elastic members 16 may be a thread type as illustrated in the drawing or a tape type with a certain width.

As the liquid pervious face sheet 11, the raw fibers for the gather non-woven fabric 15 may be synthetic fibers based on olefin such as polyethylene or polypropylene, polyester, polyamide, or reproduced fibers of rayon or cupra, natural fibers of cotton or the like. The non-woven fabric may be produced by any appropriate processing method such as spun-bonding, thermal bonding, melt-blowing, or needle punching. However, in particular, the non-woven fabric with low basis weight and high air permeability is preferably used for the three-dimensional gather sheets 15 for prevention of stuffiness. Further, the gather non-woven fabric 15 are desirably made from water-repellent non-woven fabric coated with a silicon-based, paraffin metal-based, or alkyl electrochromic chloride-based water repellent agent to prevent passage of urine or the like and rash on the wearer's body, and enhance the feel and texture (feeling of dryness).

(Structure Example of the Outer Body)

The outer body 20 in the illustrated mode constitutes integrally the front body F and the back body B. The outer body 20 has a waist part T defined as a vertical zone of the side seal portions 21 where the front body F and the back body B are joined together and an intermediate portion L defined as a front-back direction range of a portion forming the leg openings. The intermediate portion L has cover parts C positioned on width-direction both sides of the inner body 10. In a planar view, the outer body 20 has a narrower portion forming concave leg lines 29 in the front-back direction intermediate portion. The outer body 20 may constitute individually the front body F and the back body B as two divided bodies separated from each other at the crotch portion.

The outer body 20 also has an elastic sheet layer 30 and elongated elastic members 24 arranged along the width direction between a first sheet layer 20A and a second sheet layer 20B to impart elasticity in the width direction as illustrated in FIGS. 4 to 6

More specifically, the waist portion elastic members 24 are provided in a waist portion 23 of the outer body 20. The waist portion elastic members 24 are a plurality of elongated elastic members such as rubber threads arranged at vertical intervals to impart a stretching force and tighten the wearer's waist. The waist portion elastic members 24 are not arranged as a substantially single bundle at close intervals but three or more, preferably five or more members are arranged at intervals of about 3 to 8 mm to form a predetermined stretchable zone. The stretch rate of the waist portion elastic members 24 at the time of fixation can be decided as appropriate. For a general diaper for adults, the stretch rate of the waist portion elastic members 24 can be about 230 to 320%.

In the illustrated example, the waist portion elastic members 24 are rubber threads, for example. Alternatively, the waist portion elastic members 24 may be tape-like elastic members. Instead of this, the elastic sheet layer described later may be extended to the waist portion 23. The waist portion elastic members 24 in the illustrated mode are sandwiched in a folded portion 20C formed by folding the constitutional material of the second sheet layer 20B toward the inside at the waist opening edge. Alternatively, the waist portion elastic members 24 may be sandwiched between the constitutional material of the first sheet layer 20A and the constitutional material of the second sheet layer 20B.

Although there is no limitation on constitutional materials of the first sheet layer 20A and the second sheet layer 20B, non-woven fabric is used preferably from the viewpoints of air permeability and flexibility. There is no particular limitation on the raw fibers for non-woven fabric. For example, the raw fibers for non-woven fabric may be synthetic fibers based on olefin such as polyethylene or polypropylene, or synthetic fibers based on polyester, polyamide, or reproduced fibers of rayon or cupra, natural fibers of cotton or the like, or mixed fibers or composite fibers made from two or more of the foregoing fibers. Further, the non-woven fabric may be produced by any appropriate processing method. The processing method may be any one of publicly known methods such as spun-lacing, spun-bonding, thermal bonding, melt-blowing, needle punching, air-though processing, and point-bonding, for example. In the case of using the non-woven fabric, its basis weight is preferably about 12 to 20 g/m². The first sheet layer 20A and the second sheet layer 20B may be a pair of layers formed by folding back one material sheet and opposed to each other.

Figure 2:
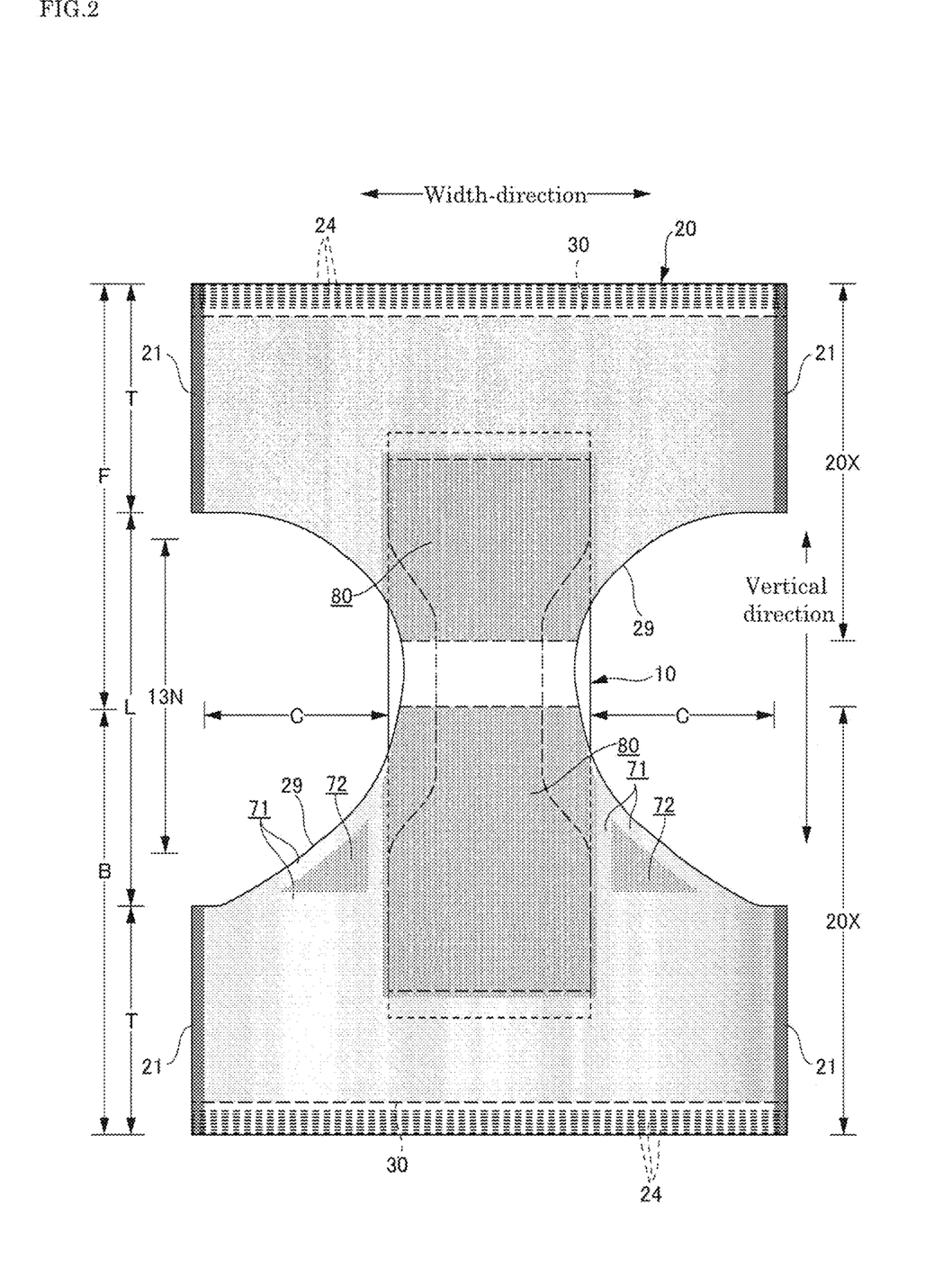
FIG. 2 is a plane view (outer surface side) of the underpants-type disposable diaper in the opened state.
Figure 3A:
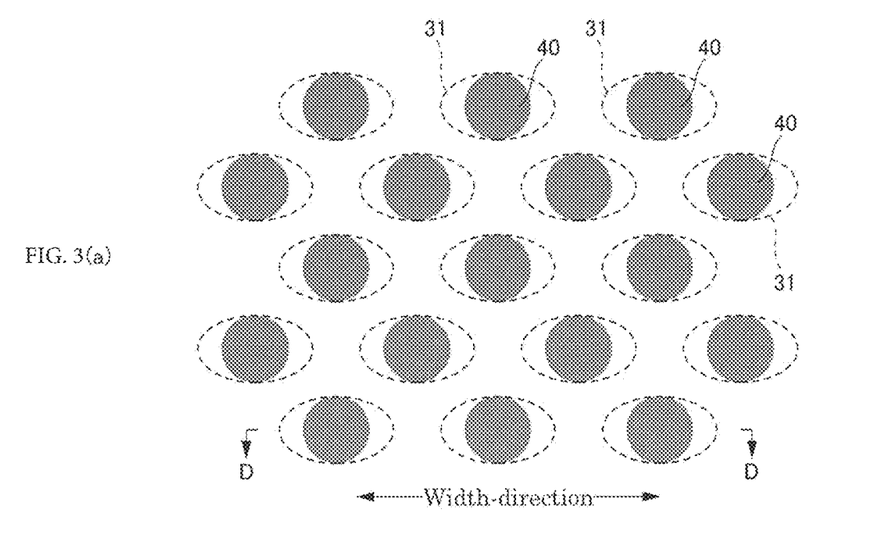
FIG. 3(a) is a plane view of major components of an outer body.
Figure 3B:
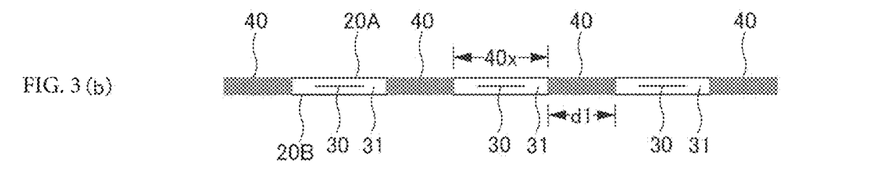
FIG. 3(b) is a cross-sectional view of FIG. 3(a) taken along line D-D.
Figure 3C:
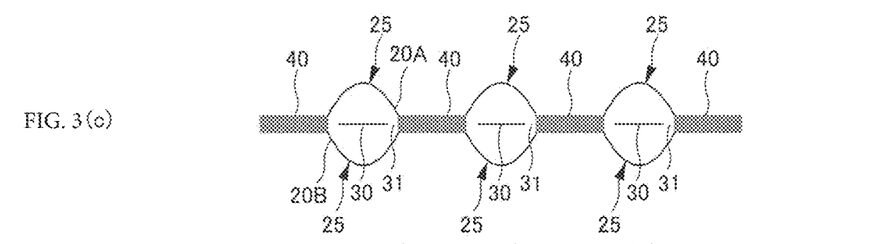
FIG. 3(c) is a cross-sectional view in a worn state.
Figure 3D:
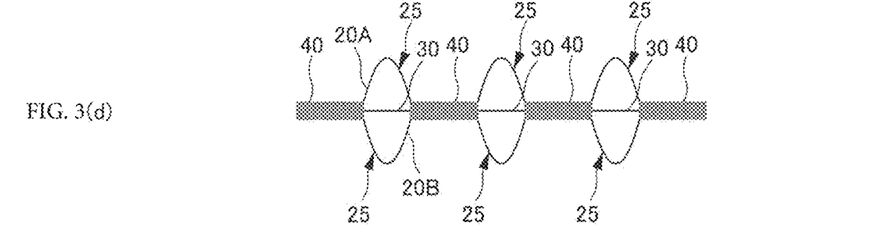
FIG. 3(d) is a cross-sectional view in a natural-length state.

In stretchable regions 20X ranging from the waist parts of the front body F and the back body B to the intermediate portion between them illustrated in FIG. 2, the elastic sheet layer 30 is stacked between the first sheet layer 20A and the second sheet layer 20B, and when the elastic sheet layer 30 is extended in the width direction, the first sheet layer 20A and the second sheet layer 20B are joined together via through holes 31 formed in the elastic sheet layer 30 by a large number of dot-like joint portions 40 arranged at intervals in the extending direction and a direction orthogonal to the extending direction, and the first sheet layer 20A and the second sheet layer 20B are not joined to the elastic sheet layer 30 at least at portions other than ones between the first sheet layer 20A and the second sheet layer 20B with the dot-like joint portions 40 as illustrated in FIG. 3. Consequently, as illustrated in FIG. 3(d), when the elastic sheet layer 30 is in the natural-length state, the first sheet layer 20A and the second sheet layer 20B between the joined portions swell to the direction of separating from each other to form contraction wrinkles 25 extending in the direction crossing the extending direction. Accordingly, as illustrated in FIG. 3(c), when the diaper is worn in the state extended to some extent in the width direction, the contraction wrinkles 25 are somewhat smoothed but left. In addition, as being understood from FIG. 3(c) illustrating the assumed worn state and FIGS. 3(a) and 3(b) illustrating the assumed completely opened state of the first sheet layer 20A and the second sheet layer 20B, in these states, there are gaps produced between through holes 31 of the dot-like joint portions in the elastic sheet layer 30 and the dot-like joint portions 40 to provide air permeability even when the material for the elastic sheet layer 30 is a non-porous film or sheet.

Characteristically, as illustrated in FIG. 2, the dot-like joint portions 40 are formed in peripheral edge regions 71 and surrounded regions 72 surrounded by the peripheral edge regions 71 in a pattern that the arrangement density of the dot-like joint portions 40 in the peripheral edge regions 71 is higher than the arrangement density of the dot-like joint portions 40 in the surrounded regions 72. In the stretchable structure in which the elastic sheet layer 30 is sandwiched in the state extended in the width direction between the first sheet layer 20A and the second sheet layer 20B and these layers are joined together by the large number of dot-like joint portions 40, the contraction rate becomes lower in the width direction with increase in the arrangement density of the dot-like joint portions 40. Accordingly, with such a change in the arrangement density, the cover parts C curve in the natural-length state such that the surrounded regions 72 swell out with respect to the peripheral edge regions 71. Even when the diaper is worn in a state extended to some extent, the curve is maintained to provide a favorable fit to the lower surface of the gluteal region. This makes it possible to improve the fit to the lower part of the gluteal even without providing elastic members along the edges 29 of the leg openings.

As understood from the principles, when at least the front-back direction intermediate portion of the cover parts C is configured such that the arrangement density of the dot-like joint portions 40 becomes higher stepwise or continuously from the width-direction outer edges to the width-direction center of the cover parts C, the cover parts C curve outward in the natural-length state. Even when the diaper is worn in the state extended to some extent, the curve is maintained to provide a fit to the lower surface of the gluteal region. In particular, it is possible to improve sufficiently the fit even in the simple structure only with the two-stage change in the arrangement density as in the illustrated mode.

Figure 10:
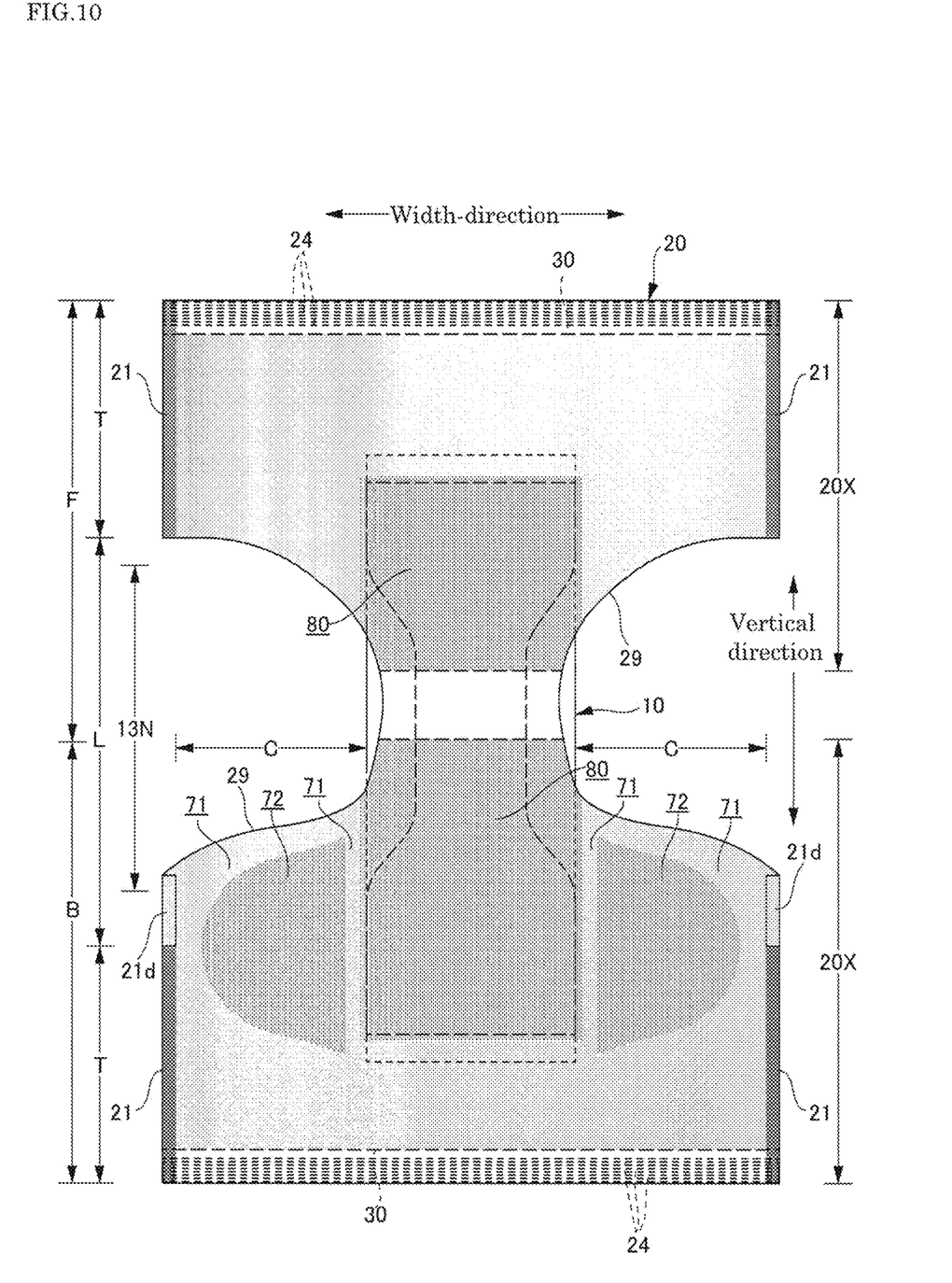
FIG. 10 is a plane view (outer surface side) of the underpants-type disposable diaper in the opened state.

The width-direction change in the density of the arranged dot-like joint portions 40 may be made in the waist part T of the back body B as well as the cover parts C as illustrated in FIG. 10, as far as the change is surely made in at least the front-back direction intermediate portion of the cover parts C. In this case, the change in the arrangement density of the dot-like joint portions 40 in the waist part T may be made continuously with respect to the change in the arrangement density of the dot-like joint portions 40 in the cover parts C as illustrated in the drawing, or may be individually made to be separate from the change in the arrangement density of the dot-like joint portions 40 in the cover parts C. By making the change in the arrangement density of the dot-like joint portions 40 in the waist part T as well, it is possible to improve the fit to only the lower part but also a wider zone of the gluteal region including the sides of the up-down intermediate portion of the gluteal region.

The width-direction outer edges of the cover parts C may be linear along the front-back direction over the entire front-back side. However, when at least the front-back direction central portion as in the mode illustrated in FIG. 8, preferably the entire front-back portion as in the mode illustrated in FIG. 2 is linear or curved toward the inner body 10 side with increasing proximity to the front-back direction central side, the fit to the lower part of the gluteal region will be more preferable with the change in the arrangement density of the dot-like joint portions 40 described above.

Figure 8:
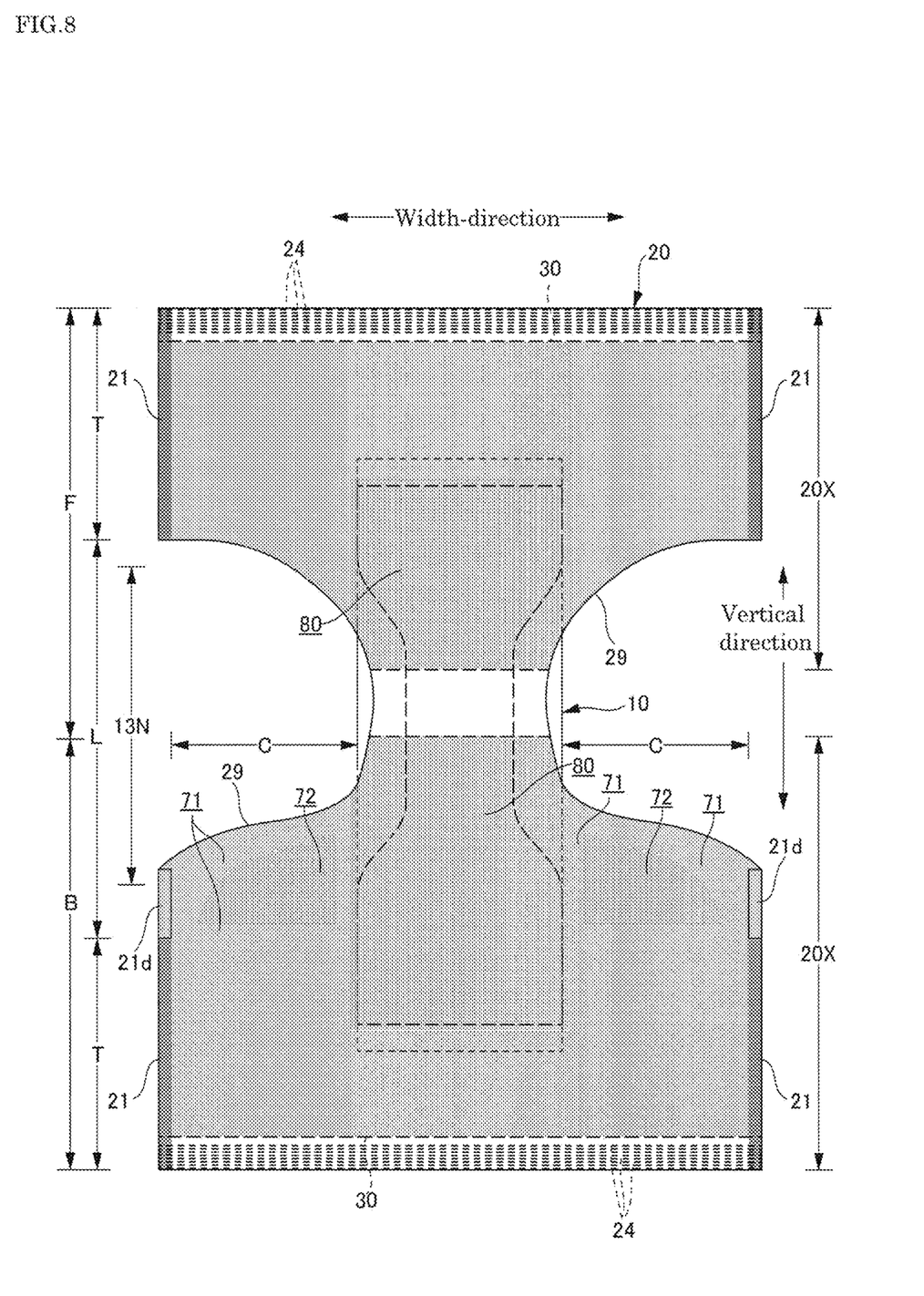
FIG. 8 is a plane view (outer surface side) of the underpants-type disposable diaper in the opened state.

In the mode in which the front-back direction length of the portions of the back body B positioned on the lateral sides of the inner body 10 is larger than the front-back direction length of the portions of the front body F positioned on the lateral sides of the inner body 10 and the cover parts C have portions on the waist part T side with the same width as the waist part T as illustrated in FIG. 8, the edges of the leg openings of the cover parts C are likely to lift and flap, where the change in the arrangement density of the dot-like joint portions 40 described above is preferably made in particular. In this mode, the side seal portions 21 are not formed on the sides of the cover parts C of the back body B, but welding traces 21d may be formed there at the time of formation of the side seal portions 21.

The difference in the arrangement density of the dot-like joint portions 40 (that is, the proportion of the dot-like joint portions 40 in the unit area) can be made by at least one of the difference in the areas of the individual dot-like joint portions 40 and the difference in the intervals between the dot-like joint portions 40. For example, when the arrangement density is to be changed in two stages as in the illustrated mode, the intervals between the dot-like joint portions 40 in high-density arrangement regions (the surrounded regions 72 in the illustrated mode, which is also applied to the following description) can be made identical to those in low-density arrangement regions (the peripheral edge regions 71 in the illustrated mode, which is also applied to the following description) and the areas of the individual dot-like joint portions 40 in the high-density arrangement regions can be made larger than those in the low-density arrangement regions, or the areas of the individual dot-like joint portions 40 in the high-density arrangement regions can be made identical to those in the low-density arrangement regions and the intervals between the dot-like joint portions 40 in the high-density arrangement regions can be made smaller than those in the low-density arrangement regions, or the areas of the individual dot-like joint portions 40 in the high-density arrangement regions can be made larger than those in the low-density arrangement regions and the intervals between the dot-like joint portions 40 in the high-density arrangement regions can be smaller than those in the low-density arrangement regions.

The areas of the individual dot-like joint portions 40 can be decided as appropriate. However, when the areas are too small, the joint is likely to be insufficient, and when the areas are too large, the hardness of the dot-like joint portions 40 exerts larger influence on the texture. Accordingly, the areas are preferably about 0.3 to 4.0 mm$^2$. In particular, when the arrangement density is to be changed in two stages as in the illustrated mode, the areas of the individual dot-like joint portions 40 in the high-density arrangement regions are preferably about 0.6 to 1.2 mm$^2$, and the areas of the individual dot-like joint portions 40 in the low-density arrangement regions are preferably about 0.3 to 0.6 mm$^2$.

Width-direction intervals 40x (opened state) between the dot-like joint portions 40 can be decided as appropriate. However, when the intervals are too large, contraction wrinkles are likely to be formed irregularly, and when the intervals are too small, the hardness of the dot-like joint portions 40 exerts larger influence on the texture. Accordingly, the intervals are preferably about 5 to 7 mm. The same thing is applied to the front-back direction intervals. In particular, the width-direction intervals 40x and the front-back direction intervals between the dot-like joint portions 40 in the high-density arrangement regions are preferably about 0.5 to 1.0 mm, and the width-direction intervals 40x and the front-back direction intervals in the low-density arrangement regions are preferably about 6 to 8 mm.

The individual dot-like joint portions 40 can have an arbitrary shape such as perfect circle, oval, polygons including triangle, star, or cloud. The size of the individual dot-like joint portions 40 can be decided as appropriate. However, when the size is too large, the hardness of the dot-like joint portions 40 exerts larger influence on the texture, and when the size is too small, the joint areas become smaller and the materials cannot sufficiently adhere to each other. Accordingly, a large diameter or diameter d1 is preferably about 0.5 to 2.5 mm.

Although there is no particular limitation on the planar arrangement of the dot-like joint portions 40, the dot-like joint portions 40 are preferably arranged in a regularly repeated pattern. The individual dot-like joint portions 40 may be repeatedly arranged on a regular basis in such a pattern as orthorhombic lattice or hexagon lattice (these are also called staggered pattern), square lattice, or rectangular lattice, parallelotope lattice (in which two groups of many obliquely parallel lines are arranged crossing each other), or groups of the dot-like joint portions 40 may be repeatedly arranged on a regular basis (the dot-like joint portions 40 in a single group may be arranged regularly or irregularly and in a pattern or a character).

There is no particular limitation on the elastic sheet layer 30, and the elastic sheet layer 30 may be formed from a plurality of materials. Alternatively, the elastic sheet layer 30 can be made from a material with elasticity such as a film-like elastic sheet made of an elastic film, and can be non-porous or have a large number of pores or slits for air permeability. The thickness of the elastic sheet layer 30 is preferably about 20 to 40 μm, although there is no particular limitation.

The stretch rate of the stretchable regions 20X (when the elastic sheet layer 30 is integrally interposed between the first sheet layer 20A and the second sheet layer 20B and is extended to the maximum degree) can be decided as appropriate, but can be about 170 to 250% in the width direction for a diaper for adults, for example. The vertical stretch rate of the stretchable regions 20X can also be decided as appropriate. However, for a diaper for adults, the vertical stretch rate can be about 100 to 125% in the mode in which the stretchable regions 20X are to be hardly extended in the vertical direction, and can be about 125 to 180% when the elastic sheet layer 30 is also vertically extended at the time of joining of the first sheet layer 20A and the second sheet layer 20B so that the stretchable regions 20X can also be extended in the vertical direction, for example.

Figure 9:
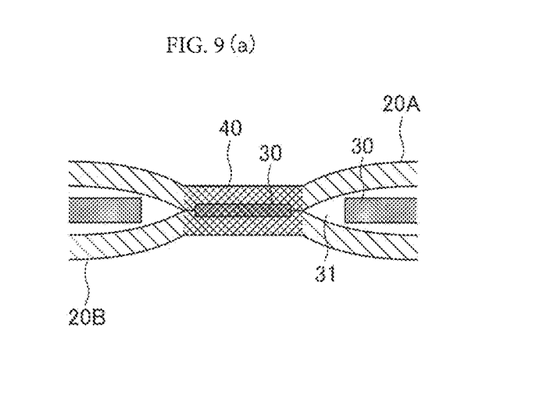
FIGS. 9(a) to 9(c) are schematic cross-sectional views of cross sections of major components of the outer body extended to some extent in a width-direction.

The first sheet layer 20A and the second sheet layer 20B may be joined together at the dot-like joint portions directly or indirectly via another sheet such as the elastic sheet layer 30. FIGS. 9(*a*) to 9(*c*) illustrate typical three kinds of joint structures. In the joint structures illustrated in FIGS. 9(*a*) and 9(*c*), the first sheet layer 20A and the second sheet layer 20B are joined together via the through holes 31 formed in the elastic sheet layer 30, and the first sheet layer 20A and the second sheet layer 20B are not joined to the elastic sheet layer 30 at least at portions other than ones between the first sheet layer 20A and the second sheet layer 20B with the dot-like joint portions 40 (the oblique lattice pattern in FIGS. 9(*a*) to 9(*c*), as in the mode illustrated in FIGS. 3(*a*) to 3(*d*). These joint structures can be produced by using the method described in JP-T No. 2004-532758 such that the arrangement pattern of raised portions on the patterned calendar roller is replaced with the pattern with the dot-like joint portions 40 and 43 in the background pattern region 70 and the display region 80. However, according to the method described in JP-T No. 2004-532758, the elastic sheet layer 30 is regarded to be pressed out without being dissolved. In that case, as illustrated in FIG. 9(*c*), the elastic sheet layer 30 may not remain between the first sheet layer 20A and the second sheet layer 20B, but the pressed pieces of the elastic sheet layer 30 not illustrated may remain movably around the through holes 31. Meanwhile, in the method described in JP-T No. 2004-532758, selecting as appropriate the kind of the material for the elastic sheet layer 30 and processing conditions such as processing temperature to allow the elastic sheet layer 30 to be dissolved and separated from the dot-like joint portions 40 would make it possible to produce the joint structure in which the dissolved and separated pieces of the elastic sheet layer 30 remain in the dot-like joint portions 40 as illustrated in FIG. 9(*a*). Accordingly, in the mode in which the dissolved and separated pieces of the elastic sheet layer 30 remain in the dot-like joint portions 40 between the first sheet layer 20A and the second sheet layer 20B, it can be said that the first sheet layer 20A and the second sheet layer 20B are joined to the elastic sheet layer 30 at the dot-like joint portions 40, but the first sheet layer 20A and the second sheet layer 20B are surely not joined to the elastic sheet layer 30 at the portions other than at least the ones between the first sheet layer 20A and the second sheet layer 20B with the dot-like joint portions 40 (which means that the first sheet layer 20A and the second sheet layer 20B at the dot-like joint portions 40 are not joined to the elastic sheet layer 30 around the dot-like joint portions 40 (that is, the edges of the through holes 31). As a matter of course, in the manufacturing method described in JP-T No. 2004-532758, selecting as appropriate the kind of the material for the elastic sheet layer 30 and processing conditions such as processing temperature so as not to dissolve or separate the elastic sheet layer 30 from the dot-like joint portions 40 or form the through holes 31 would make it possible to produce the joint structure in which no through holes are formed in the elastic sheet layer 30 at the dot-like joint portions 40 but the first sheet layer 20A and the second sheet layer 20B are joined together indirectly via the elastic sheet layer 30 as illustrated in FIG. 9(b).

In the illustrated example, the elastic sheet layer 30 is interposed in the stretchable regions 20X of the outer body 20 except the waist portion. Alternatively, the elastic sheet layer 30 may be interposed up to the waist portion to eliminate the elongated resilient and elastic members, or the elastic sheet layer 30 may not be provided at the waist part T but the elongated resilient and elastic members may be provided at the waist part as well as the waist portion.

The elastic sheet layer 30 is desirably arranged in the region of the underpants-type disposable diaper overlapping the absorber 13 for the manufactural reason but no elasticity is actually needed in that region. Accordingly, in a preferred mode as in the illustrated example, the arrangement density is increased in the regions 80 of large parts (entire or partial parts) of the stretchable regions 20X of the outer body 20 overlapping the absorber 13 to make contraction wrinkles 25 smaller, that is, decrease the amount of contraction.

(Front and Back Pressing Sheets)

Figure 1:
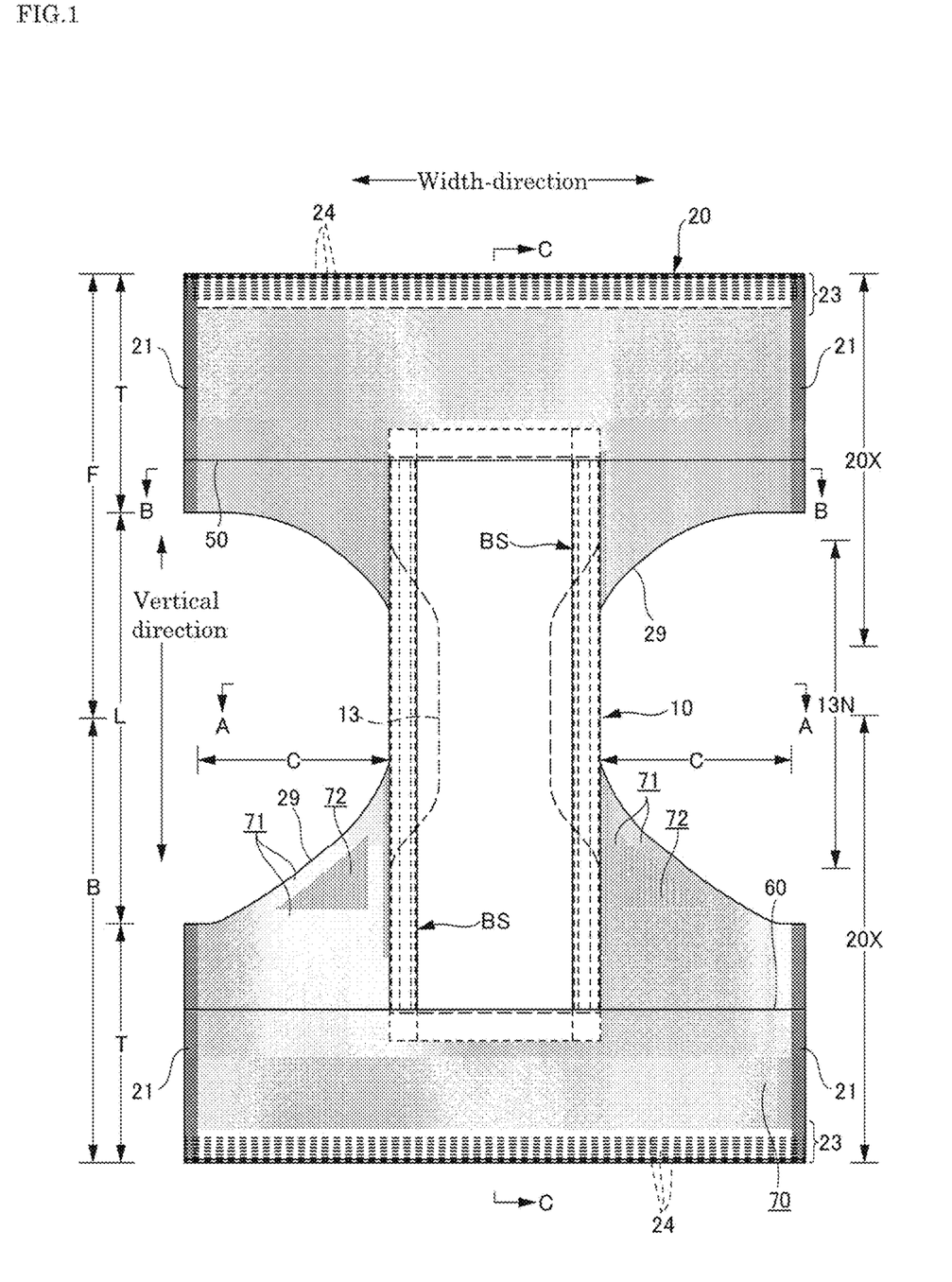
FIG. 1 is a plane view (inner surface side) of an underpants-type disposable diaper in an opened state.

As also illustrated in FIGS. 1 and 4, front and back pressing sheets 50 and 60 may be provided to cover the front and back end portions of the inner body 10 on the inner surface of the outer body 20 and prevent leakage from the front and back edges of the inner body 10. The illustrated mode will be described more in detail. The front pressing sheet 50 extends on the inner surface of the front body F in the width direction entirely from the inner surface of the folded portion 20C at the waist-side end to the part overlapping the front end part of the inner body 10. The back pressing sheet 60 extends on the inner surface of the back body B in the width direction entirely from the inner surface of the folded portion 20C at the waist-side end to the part overlapping the back end part of the inner body 10. The front and back pressing sheets 50 and 60 can have small non-bonded portions at the entire crotch lower side edges in the width direction (or only at the central portion) to prevent the adhesive from squeezing out and allow the non-bonded portions to lift slightly from the face sheet and serve as leak prevention walls.

Attaching the front and back pressing sheets 50 and 60 as separate members as in the illustrated mode would provide the advantage of a higher degree of freedom of material selection but also provide the disadvantage of increase in the numbers of materials and manufacturing processes. Accordingly, the folded portions 20C formed by folding the outer body 20 toward the inside of the diaper may be extended up to the parts overlapping the inner body 10 to form the parts equivalent to the pressing sheets 50 and 60.

<Description of Terms Used Herein>

Unless otherwise specified herein, the terms used herein have the meanings described below.

The "stretch ratio" refers to a value with respect to 100% representing the natural length.

The "basis weight" is measured in such a manner as described below. That is, a sample or a test piece is preliminarily dried and left to stand in a test room or a test device in a standard state (at a temperature of 20±5° C. and a relative humidity of 65% or less) until it reaches a constant weight. The preliminary drying refers to turning the sample or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) sample by the use of a cutting template (200 mm×250 mm±2 mm). The weight of the sample is measured and the measured value is multiplied by 20 to determine the weight per square meter as a basis weight.

The "thickness" is automatically measured by an automated thickness gauge (KES-G5 handy compression measurement program) on the conditions that the load is 10 gf/cm$^2$ and the pressure area is 2 cm$^2$).

The present invention is applicable to the underpants-type disposable diapers as in the example described above.

REFERENCE SIGNS LIST

B Back body
F Front body
Inner body
Liquid pervious face sheet
Liquid impervious back sheet
Absorber
Package sheet
Gather non-woven fabric
Gather elastic member
Outer body
20C Folded portion
Side seal portion
Waist portion elastic member
Leg line
13N Narrower part
20A First sheet layer
20B Second sheet layer
Elastic sheet layer
Dot-like joint portion
Contraction wrinkle
20X Stretchable region
C Cover part
T Waist part
L Intermediate portion
Peripheral edge region
Surrounded region

The invention claimed is:

1. An underpants-type disposable diaper comprising an outer body constituting individually or integrally a front body and a back body, and an inner body including an absorber provided on an inner side of the outer body ranging from the front body to the back body, the outer body of the front body and the outer body of the back body being joined together at side edges to form side seal portions, thereby forming a waist opening and a pair of right and left leg openings, wherein the outer body of the back body has a waist part defined as a front-back direction range having the side seal portions and an intermediate portion defined as the front-back direction range forming the leg openings, the intermediate portion has cover parts positioned closer to lateral sides of the inner body, the cover parts are formed at least by stacking an elastic sheet layer between a first sheet layer and a second sheet layer, when the elastic sheet layer is extended in a width-direction, the first sheet layer and the second sheet layer are joined together directly or indirectly at a large number of dot-like joint portions arranged at intervals left in the width-direction and front-back direction, and at least the intermediate portion of the cover parts in the front-back direction are configured such that an arrangement density of the dot-like joint portions becomes higher stepwise or continuously from width-direction outer edges to a width-direction central side.

2. The underpants-type disposable diaper according to claim 1, wherein the cover parts have peripheral edge regions and surrounded regions surrounded by the peripheral edge regions, and the arrangement density of the dot-like joint portions in the peripheral edge regions is higher than the arrangement density of the dot-like joint portions in the surrounded regions.

3. The underpants-type disposable diaper according to claim 2, wherein the width-direction outer edges of the cover parts, and outer edges of at least a front-back direction central side of the cover parts are linear or curved so as to be positioned closer to the inner body with increasing proximity to the front-back direction central side.

4. The underpants-type disposable diaper according to claim 1, wherein a front-back direction length of parts of the back body positioned on the lateral sides of the inner body is larger than a front-back direction length of parts of the front body positioned on the lateral sides of the inner body, and the cover parts have portions of the same width as the waist part on a waist part side.

5. The underpants-type disposable diaper according to claim 1, wherein at least a front-back direction intermediate portion of the waist part of the outer body of the back body is configured such that the arrangement density of the dot-like joint points becomes higher stepwise or continuously from a width-direction outer edge to the width-direction central side.

6. The underpants-type disposable diaper according to claim 1, wherein a difference in the arrangement density of the dot-like joint portions is made by at least one of a difference in the areas of individual dot-like joint portions and a difference in intervals between the dot-like joint portions.

* * * * *